United States Patent
Adaikan et al.

(10) Patent No.: US 6,548,544 B1
(45) Date of Patent: Apr. 15, 2003

(54) METHOD OF TREATMENT OF PRIAPISM WITHOUT RAISING SYSTEMIC BLOOD PRESSURE

(75) Inventors: Periannan Adaikan, Singapore (SG); Soon Chye Ng, Singapore (SG)

(73) Assignee: The National University of Singapore (SG)

( * ) Notice: Subject to any disclaimer, the term of this patent is extended or adjusted under 35 U.S.C. 154(b) by 0 days.

(21) Appl. No.: 09/714,614

(22) Filed: Nov. 17, 2000

(30) Foreign Application Priority Data

Nov. 18, 1999 (SG) ............................................... 9905846

(51) Int. Cl.[7] .............................................. A61K 31/20
(52) U.S. Cl. ...................................................... 514/559
(58) Field of Search ......................................... 514/559

(56) References Cited

U.S. PATENT DOCUMENTS 5,474,535 A * 12/1995 Place et al.
5,773,020 A    6/1998 Place et al.
6,036,977 A * 3/2000 Drizen et al.

FOREIGN PATENT DOCUMENTS

WO   WO 93/00894    1/1993
WO   WO 99/02147    1/1999

OTHER PUBLICATIONS

Boyle et al., J. Urol., 143: 933–935 (1990).
Brindley, Lancet, 2(8396) : 220–221 (1984).
Steers et al., J. Urol., 146: 1361–1363 (1991).
Wilson et al. J. Pharmacol Exp ther 1975;195(3):565–576.*
Clark et al. Prostaglandins, 1981;22(3):333–348.*

* cited by examiner

Primary Examiner—Sreeni Padmanabhan
Assistant Examiner—San-ming Hui
(74) Attorney, Agent, or Firm—Birch, Stewart, Kolasch & Birch, LLP

(57) ABSTRACT

Treatment or prophylaxis of persistent penile erection resulting from, for example, physiological dysfunction, trauma, surgical intervention, or chemical induction. The method of the present invention is practiced by the administration of an agent capable of inducing, promoting, or otherwise facilitating contraction of the cavernosum. Another aspect of the present invention provides a composition comprising a cavernosum contraction-inducing, -promoting, or -facilitating agent. In one embodiment, the agents of the present invention are prostaglandins or functional derivatives, homologous, analogues, agonists, mimetics, or metabolites thereof. This invention also provides a means for diagnosing the physiological basis behind penile dysfunction.

6 Claims, 2 Drawing Sheets

METHOD OF TREATMENT OF PRIAPISM WITHOUT RAISING SYSTEMIC BLOOD PRESSURE

FIELD OF THE INVENTION

The present invention relates generally to the treatment and prophylaxis of penile dysfunction. More particularly, the present invention contemplates the treatment and prophylaxis of persistent penile erection resulting from, for example, physiological dysfunction, trauma, surgical intervention, or chemical induction. The method of the present invention is practised by the administration of an agent capable of inducing, promoting or otherwise facilitating contraction of the cavernosum. Accordingly, another aspect of the present invention provides a composition comprising a cavernosum contraction-inducing, -promoting, or -facilitating agent. In one embodiment, the agents of the present invention are prostaglandins or functional derivatives, homologues, analogues, agonists, mimetics, or metabolites thereof. This invention also provides a means for diagnosing the physiological basis behind penile dysfunction.

BACKGROUND OF THE INVENTION

Priapism is defined as a prolonged, usually painful, penile erection generally not directly initiated by sexual stimulus. It results from a disturbance or other dysfunction in the normal regulatory mechanisms which initiate and maintain penile flaccidity. The treatment of this condition ranges from predominately surgical management to less invasive pharmacological therapies. Despite recent advances in the understanding of erectile mechanisms, the pathophysiology of priapism remains obscure in up to 50% of cases. See, e.g., Steers and Selby, *J. Urol.* 146(5): 1361–1363 (1991). Thus, in the absence of an identifiable aetiology, treatment has been essentially symptomatic. In at least 5% of patients treated for impotence, injection of vasoactive substances such as papaverine, prostagiandin E, and phenoxybenzamine (or phentolamine), an alpha-adrenergic blocking drug, into the corpora cavernosa muscle, is the most likely cause of priapism. Furthermore, the availability of sildenafil citrate (sold under the trademark "Viagra") as an anti-impotence drug, has resulted in its misuse as an aphrodisiac to improve male sexual performance. Reports indicate that sildenafil also has caused priapism. If left unattended, the abuse and misuse of erection-producing vasoactive agents is likely to lead to priapism and irreversible muscle damage. Other situations in which priapism is seen include disease states such as sickle cell anaemia and use of unrelated drugs such as antidepressants (e.g., trazodone).

Current antidotes for priapism are alpha-adrenoceptor agonists such as metaraminol, adrenaline, phenylephrine, noradrenaline, and ethylephrine. These alpha-mimetics are known to produce systemic side effects including a rise in systemic blood pressure. Hence, such agents are contraindicated for cardiovascular patients. Accordingly, there is a need to identify reliable, safe, and efficacious pharmacological agents for the treatment and prophylaxis of penile dysfunction characterized by prolonged penile erection.

SUMMARY OF THE INVENTION

The present invention is predicated in part on the identification of a group of compounds which induce, promote, or otherwise facilitate contraction of the cavernosum associated with penile tissue. An important feature of this invention is that the agents employed in accordance with the present invention do not cause a rise in systemic blood pressure. Particularly preferred agents include the prostaglandins such as, but not limited to, prostaglandin A2, prostaglandin A1, prostaglandin B1, and prostaglandin B2, as well as functional derivatives, homologues, analogues, agonists, mimetics, and metabolites thereof.

Accordingly, one aspect of the present invention contemplates a method for the treatment or prophylaxis of priapism in a male subject, said method comprising administering to said subject an effective amount of an agent which induces, promotes or otherwise facilitates contraction of corpora cavernosa muscle in the cavernosum, without a concomitant rise in systemic blood pressure, the administration of which agent leads to partial or complete penile flaccidity.

Another aspect of the present invention is directed to a method for the treatment or prophylaxis of priapism in a male subject said method comprising administering to said subject an effective amount of a prostaglandin or a functional derivative, homologue, analogue, agonist, mimetic, or metabolite thereof which induces, promotes, or otherwise facilitates contraction of corpora cavernosa muscle in the cavernosum, without a concomitant rise in systemic blood pressure, for a time and under conditions sufficient to lead to partial or complete penile flaccidity or to prevent or reduce the likelihood of an erection.

Yet another aspect of the present invention provides a composition for pharmaceutical use comprising an agent which induces, promotes, or otherwise facilitates contraction of corpora cavernosa muscle in the cavernosum in penile tissue, said composition further comprising one or more pharmaceutically acceptable carriers and/or diluents.

The preferred agents of the present invention are prostaglandins such as, but not limited to, prostaglandin A2, A1, B1, and B2.

The most preferred agent is prostaglandin A2 or functional derivatives, homologues, analogues, agonists, mimetics, or metabolites thereof. The terms "prostaglandin A2", "Adainus", "AS-8", and "priapres" may be used interchangeably to refer to "prostaglandin A2".

DETAILED DESCRIPTION OF THE INVENTION

Figure 1:
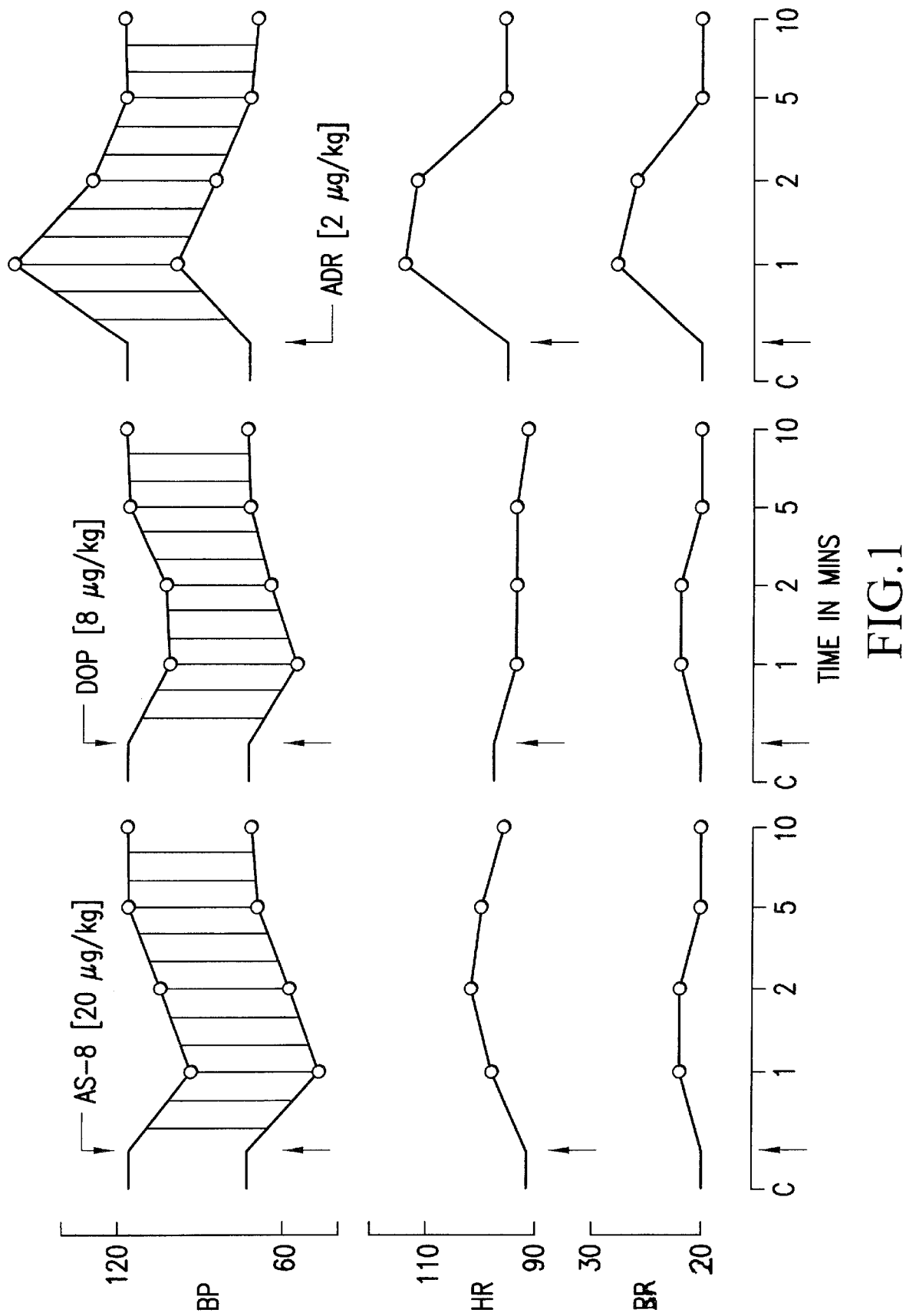
FIG. 1 is a graphical representation showing the effect of intravenous bolus dosages of prostaglandin A2 on blood pressure, heart rate, and respiratory rate in anaesthetised baboons.

In accordance with the present invention, agents which are useful in the treatment of priapism have been identified. The agents of the present invention differ from known priapism-treating agents, such as alpha-adrenoceptor agonists, in that the present agents do not cause systemic side effects such as tachycardia or raised blood pressure. Such side effects render these known therapeutic contraindicated for cardiovascular patients.

The preferred agents of the present invention are prostaglandins including functional derivatives, homologues, analogues, agonists, mimetics, or metabolites thereof.

The preferred prostaglandins of the present invention are prostaglandin A2, prostaglandin A1, prostaglandin B1, and prostaglandin B2. The most preferred prostaglandin is prostaglandin A2.

Accordingly, one aspect of the present invention contemplates a method for the treatment or prophylaxis of priapism in a male subject, said method comprising administering to said subject an effective amount of an agent which induces, promotes, or otherwise facilitates contraction of corpora cavernosa muscle in the cavernosum, without a concomitant rise in systemic blood pressure, the administration of which agent leads to partial or complete penile flaccidity. Standard $ED_{50}$ measurements, dose-response curves, bioassay methods, and the like can be used by those skilled in the art to evaluate contractile potency.

Reference herein to "priapism" includes and encompasses prolonged or sustained penile erection. Generally, priapism does not result from sexual stimulation. However, the present invention includes the treatment of prolonged penile erection following sexual stimulation. Priapism may result from surgical intervention, trauma, physiological dysfunction, or pharmacological intervention, such as following the ingestion or administration of drugs (e.g., sildenafil citrate, papaverine, or phenoxylbenzamine). Priapism may also result from disease states, from use of some drugs not related to erectile function/dysfunction, or may be spontaneous unexplained priapism.

The present invention extends to treating a subject having an erection or preventing or at least reducing the likelihood of a subject obtaining an erection. Accordingly, the present invention extends beyond priapism to the treatment of hypersexual stimulation. This may be useful in treating certain classes of habitual sex offenders.

Although the present invention is directed mainly at the treatment in human males, it also has an application in the veterinary field. For example, difficulties may arise for male stud animals such as stud bulls, horses, sheep, and pigs. Such animals may need to be chemically sexually aroused in order to produce semen or to service female animals. To induce a non-aroused state after service, the agents of the present invention may be administered to the male animal.

Another aspect of the present invention is directed to a method for the treatment or prophylaxis of priapism in a male subject, said method comprising administering to said subject an effective amount of a prostaglandin or a functional derivative, homologue, analogue, agonist, mimetic, or metabolite thereof which induces, promotes, or otherwise facilitates contraction of corpora cavernosa muscle in the cavernosum, without a concomitant rise in systemic blood pressure, for a time and under conditions sufficient to lead to partial or complete penile flaccidity or to prevent or reduce the likelihood of an erection.

Reference herein to "prostaglandin" and in particular prostaglandin A2, A1, B1, and/or B2 includes reference to functional derivatives, homologues, analogues, agonists, mimetics, or metabolites thereof. Derivatives and analogues will include those involving substitution at the 9 and 11 positions in the ring structure and those including changes in the degree of side chain unsaturation. Metabolites include, for instance, 15-oxo PGA2, 13,14-dihydro PGA2, and 13,14-dihydro-15-oxo PGA2, and the corresponding metabolites of PGA1, PGB1, and PGB2. The term "functional" means that the molecule behaves in substantially the same therapeutic manner, inducing flaccidity without inducing any substantial change in blood pressure, as the "parent" prostaglandin, i.e., the prostaglandin prior to modification.

The prostaglandin or other compound useful in the practice of the present invention is usefully formulated in the form of a pharmaceutical composition. Accordingly, another aspect of the present invention provides a composition for pharmaceutical use comprising an agent which induces, promotes, or otherwise facilitates contraction of corpora cavernosa muscle in the cavernosum in penile tissue. These compositions further comprise one or more pharmaceutically acceptable carriers and/or diluents. The compositions of the present invention may comprise the prostaglandin alone or it may be in combination with other therapeutic agents.

As indicated above, the preferred agent is a prostaglandin such as prostaglandin A2, A1, B1, or B2. The most preferred agent is prostaglandin A2 or its functional derivative, homologue, analogue, agonist, mimetic, or metabolite.

A preferred dosage range for these agents in accordance with this invention is from 1 to 10, more preferably 0.5 to 2.5, micrograms per kilogram of patient body weight.

The composition of the present invention may be administered in any convenient manner such as, but not limited to, intravenous injection, intramuscular injection, intrarectal, intranasal, subcutaneous injection, transdermal, transurethral, intraperitoneal, or oral administration. Administration may also be via patch, intravenous drip, spray, or during surgery or other invasive procedure. The most effective administration is via injection into the corpus cavernosa. This is referred to as intracavernous drug delivery.

The identification of prostaglandins as an effective treatment of priapism provides a means for identifying physiological causes for conditions such as impotence, hypersexuality, and priapism. For example, impotent males may produce excessive amounts of particular prostaglandins. Alternatively, reduced prostaglandin production or local levels may be indicated in priapism patients. The identification of levels of particular prostaglandins provides one level of diagnosis for penile dysfunction. Such methods of diagnosis are contemplated by the present invention.

Accordingly, another aspect of the present invention contemplates a method for diagnosing the physiological basis behind priapism in a male subject, said method comprising determining the level in said subject of prostaglandin A2, A1, B1, and/or B2 or derivatives and/or metabolites thereof, wherein low levels of one or more of said prostaglandin is indicative of a causative effect for priapism.

Yet another aspect of the present invention is directed to the use of a prostaglandin or a functional derivative, homologue, analogue, agonist, mimetic, or metabolite thereof in the treatment of priapism in a male subject.

The present invention is further described by the following non-limiting Examples.

EXAMPLE 1

Effects of Adainus on Pharmacologically Induced Prolonged Erection (Pipe)

Six male baboons weighing between 8 kg and 12 kg were used for the experiment. The animals were sedated with ketamine and anaesthetised with intravenous pentobarbitone injected through an indwelling venous catheter. Drugs were injected into the right corpora cavornosa at the mid-third of the shaft using a 29G needle and 1 ml syringe. Blood pressure was monitored through a cannulated femoral artery connected to the transducer. A measuring tape was used to measure penile length visually from a marked point at the base of the penis to the tip of urethral orifice. Changes in penile length were recorded for a period of 100 min after injection.

Intracavernous injection of papaverine (40 mg) or phenoxybenzamine (3 mg) which produced maximal penile length within 20 and 40 min were repeated one week later and prostaglandin A2 was given at the peak time of the turgidity.

In human patients and human volunteers, intracavernous injection of prostaglandin A2 (150 µg) was tested on prolonged erection (lasting more than 4 hours) induced by 60 mg of papaverine.

EXAMPLE 2

Response to Adainus (Prostaglandin A2)

In baboons, intracavernous injection of papaverine (40 mg) or phenoxybenzamine (3 mg) produced a 130% increase in penile length within 10 min after administration (Table 1). This increase in penile length lasted for more than 100 min. This was repeated one week later and when prostaglandin A2 was injected intracavernosally at the maximum rigidity 20 min after the drug administration, the latter produced a marked reduction in penile length and within 40 min of injection, the penile size reduced to the original state of rugosity (Table 1). The fall in systemic blood pressure produced by prostaglandin A2 ranged from 8 to 16 mmHg. Each value reported in Table 1 represents the mean of six experiments.

TABLE 1

Effect of AS-8 on Papaverine- and Phenoxybenzamine-Induced Prolonged Erection (PIPE) in Baboons

| | Minutes after injection | | | | | | | | |
|---|---|---|---|---|---|---|---|---|---|
| | 1 | 2 | 5 | 10 | 20 | 40 | 60 | 80 | 100 |
| | Mean Change in Penile Length (% of Control) | | | | | | | | |
| Papaverine (40 mg) One week later | 30 | 40 | 52 | 130 | 130 | 130 | 130 | 130 | 130 |
| Papaverine (40 mg) followed by AS-8 (100 µg) 20 min later | 32 | 38 | 65 | 130 | 142 | 15 | 0 | 0 | 0 |
| Phenoxybenzamine (3 mg) One week later | 10 | 15 | 15 | 48 | 80 | 120 | 120 | 120 | 120 |
| Phenoxybenzamine (3 mg) followed by AS-8 (100 µg) 20 min later | 7 | 15 | 20 | 38 | 85 | 10 | 0 | 0 | 0 |

Intracavernous injection of prostaglandin A2 (150 µg) readily reduced the penile length in patients and volunteers who were having prolonged erection induced by 60 mg of papaverine for 4 hours or more. Maximal reduction in rigidity and penile length to the rugose state was achieved within 30 min after injection of prostaglandin A2 in four out of five subjects. In one volunteer, there was a relapse of tumescence within 60 min after the first injection of prostaglandin A2 (150 µg). This was corrected by an additional injection of prostaglandin A2 (100 µg). The fall in mean systemic blood pressure ranged from 7 to 10 mmHg (Table 2).

TABLE 2

| Mean Decrease in Length of Turgid Penis % | | | | | |
|---|---|---|---|---|---|
| Minutes after AS-8 injection | 1 | 5 | 10 | 20 | 30 |
| Patients (2) | 10 | 50 | 80 | 90 | 100 |
| Volunteers (3) | 10 | 30 | 75 | 80 | 95 |

EXAMPLE 3

Outcome

The present study indicates that administration of prostaglandin A2 is an efficient alternative to metaraminol or adrenaline in correcting pharmacologically induced prolonged erection in man. Unlike the sympathomimetic compounds that raise the systemic blood pressure (FIG. 1), intracavernous injection of 100 to 150 µg of prostaglandin A2 produced a pressure fall of 7 to 16 mmHg in the baboon and man.

Figure 2:
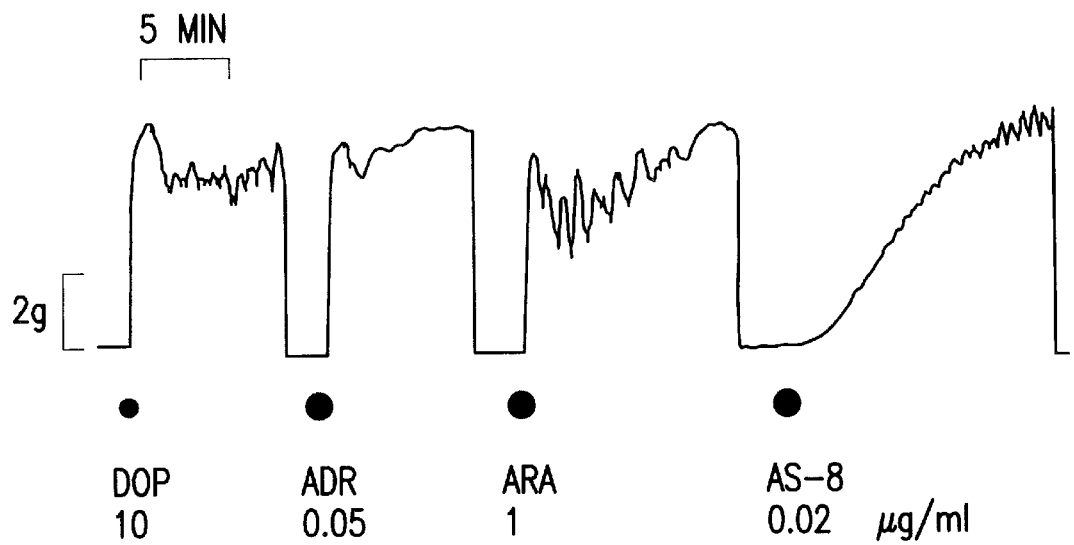
FIG. 2 is a graphical representation showing contractile response of prostaglandin A2 on human corpus cavernosum smooth muscle.

This mild fall in blood pressure produced by the administration of prostaglandin A2 suggest a dilatation of vasculature facilitating penile engorgement. Subjective observation in the present study, both in the baboon and man indicates that the marked contractile property of prostaglandin A2 on the corpora cavenosa muscle probably dominates this effect in reversal to PIPE. Prostaglandin A2 is 8.2 times stronger than noradrenaline in contracting human corpora cavernosa muscle in vitro and 500, 2.5 and 50 times stronger than dopamine, adrenaline and aramine, respectively (FIG. 2). The results also suggest that if prostaglandin A2 exists physiologically (especially in excessive amounts) then this might contribute to detumescence or non-erectile state of the penis more readily than noradrenaline.

EXAMPLE 4

Other Prostaglandins

Testing of prostaglandins A1, B1, and B2 using the above protocol will demonstrate that these prostaglandins are also effective in inducing, promoting, or otherwise facilitating contraction of the cavernosum but are not as active as prostaglandin A2.

EXAMPLE 5

Effect of Adainus (AS-8) on Intracavernous Pressure (ICP) Response in an in vivo Rat Model The cavernous nerve is a relatively well-defined nerve that exits from the major pelvic ganglion and carries a large component of the autonomic input to the penis. Through electrical stimulation of this nerve, the changes in the peripheral neural mechanisms controlling penile erection can be observed in the animal model. The responses are recorded as concomitant alterations in the ICP following stimulation of this nerve branch.

METHOD: Male Sprague Dawley rats (500–700 g) were anaesthetized with sodium pentobarbital (45 mg/kg, intraperitoneal) and the trachea intubated (14G jelco catheter) for respiration. The left external jugular vein and the right common carotid artery were cannulated (PE 50 tubing) for drug infusion and blood pressure monitoring respectively. Through a lower median abdominal incision, the lateral prostate was exposed and the fascia around the cavernous nerve separated through fine dissection. The exposed nerve was suspended on bipolar hook electrode for stimulation. Through transverse perineal incision, a 27G needle was inserted into the penile crus for pressure recording. Systemic and intracavernous pressures were measured by transducers (Ugo Basile) and recorded with MacLab analogue-digital converter (AD instruments). To initiate the experiment, the cavernous nerve was stimulated with square wave pulses of 1 millisecond duration at 20 Hertz and 2 volts with the resting ICP recording. The stimulation was repeated following intracavernous administrations of 1, 2 and 4pg of AS-8 with saline administration as control.

Figure 3:
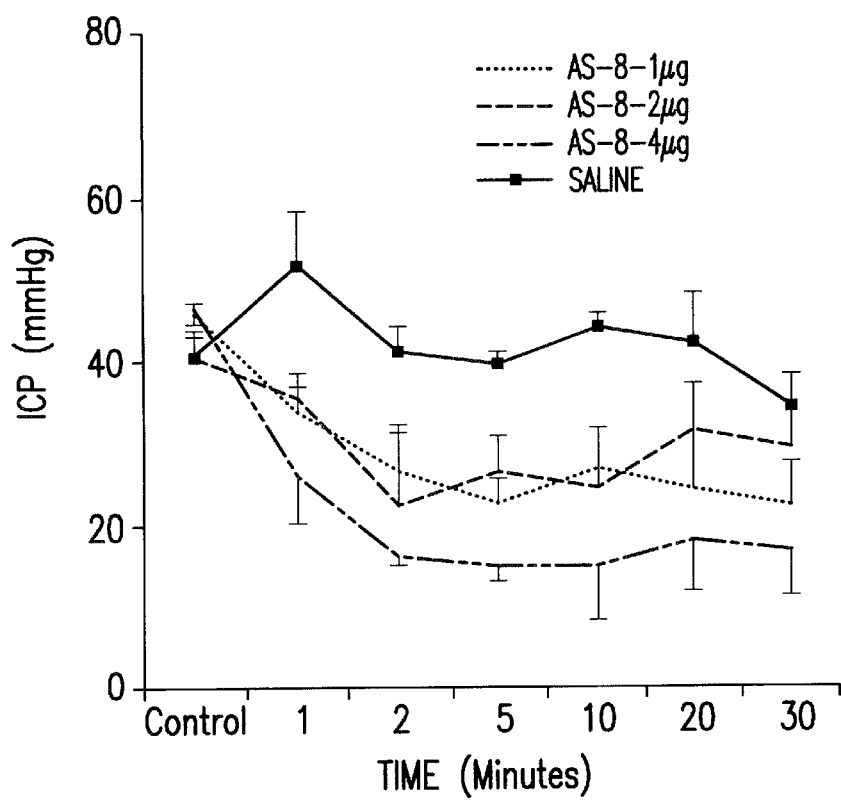
FIG. 3 is a graphical representation showing cavernous pressure before and after saline and AS-8 administration.

RESULTS: Stimulation of cavernous nerve induced a rapid pressure increase and tumescence in the saline and drug-treated rats before AS-8 (Control recording) administration. Following intracavernous AS-8, the cavernous pressure elevations to subsequent nerve stimulations were significantly suppressed (Analysis of Variance: multivariate and one way) at all the doses tested and this was accompanied by concurrent reduction in mean systemic blood pressure in these animals (Tables 3 and 4; FIG. 3).

TABLE 3

Cavernous pressure (mmHg) recording before (Control) and after (Saline and AS-8) administration

| TIME | AS-8 1 $\mu$g | AS-8 2 $\mu$g | AS-8 4 $\mu$g | SALINE |
|---|---|---|---|---|
| Control | 45.76 ± 1.46 | 40.60 ± 2.58 | 46.40 ± 1.59 | 40.77 ± 3.21 |
| 30 Sec | 33.83 ± 3.09* | 35.29 ± 3.29 | 25.91 ± 5.57* | 51.95 ± 6.53 |
| 2 Min | 26.48 ± 4.62* | 22.29 ± 9.96* | 16.07 ± 1.00* | 41.49 ± 2.74 |
| 5 Min | 22.48 ± 3.21* | 26.42 ± 4.42* | 14.90 ± 1.71* | 39.94 ± 1.02 |
| 10 Min | 26.94 ± 4.77 | 24.49 ± 7.39 | 15.00 ± 6.71* | 44.56 ± 1.47 |
| 20 Min | 24.42 ± 6.87* | 31.84 ± 5.54 | 18.30 ± 6.40* | 42.71 ± 5.67 |

TABLE 3-continued

Cavernous pressure (mmHg) recording before (Control) and after (Saline and AS-8) administration

| TIME | AS-8 1 $\mu$g | AS-8 2 $\mu$g | AS-8 4 $\mu$g | SALINE |
|---|---|---|---|---|
| 30 Min | 22.40 ± 5.34 | 29.62 ± 4.62 | 17.05 ± 5.86 | 34.74 ± 3.82 |

*$P < 0.05$

TABLE 4

Mean systemic blood pressure (mmHg) recording before (Control) and after Saline and AS-8 administration

| TIME | AS-8 1 $\mu$g | AS-8 2 $\mu$g | AS-8 4 $\mu$g | SALINE |
|---|---|---|---|---|
| Control | 96.86± 9.13 | 100.42± 5.67 | 105.63± 10.11 | 102.12± 3.29 |
| 30 Sec | 92.30± 15.96 | 84.64± 13.73 | 84.74± 13.53 | 103.36± 14.90 |
| 2 Min | 92.36± 11.41 | 68.87± 3.39 | 84.72± 19.05 | 105.47± 10.23 |
| 5 Min | 80.57± 6.35 | 88.12± 13.25 | 81.53± 19.22 | 93.70± 0.44 |
| 10 Min | 90.90± 5.79 | 91.31± 14.25 | 89.63± 18.09 | 103.83± 2.44 |
| 20 Min | 78.15± 10.08 | 88.48± 15.48 | 85.51± 15.97 | 111.13± 2.55 |
| 30 Min | 72.45± 6.21 | 90.00± 16.14 | 84.73± 7.68 | 111.83± 2.59 |

It can be seen that Adainus prevents, in a dose-dependent manner, the intracavernous pressure increase (indicative of penile erection) to cavernous nerve stimulation. This acute study conclusively establishes the therapeutic potential of Adainus in interfering with nerve-mediated penile tumescence and rigidity. Coupled with the reversal of drug-induced penile erection in baboons and the potent in vitro contractile effect observed earlier, this clearly suggests its usefulness in priapism.

Throughout this specification, unless the context requires otherwise, the word "comprise" and variations such as "comprises" or "comprising" will be understood to imply the inclusion of a stated element or integer or group of elements or integers but not the exclusion of any other element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A method for the treatment of priapism in a male subject suffering from priapism without raising the systemic blood pressure of said subject comprising
   administering to said subject an amount of a pharmaceutical composition comprising a prostaglandin A1, prostaglandin B1, prostaglandin B2, or prostaglandin A2 in an amount which facilitates contraction of corpora cavernosa muscle in the cavernosum, without a concomitant rise in systemic blood pressure, whereby the subject experiences penile flaccidity.

2. The method of claim 1, wherein the prostaglandin is prostaglandin A2.

3. The method of claim 1, wherein the agent is intracavernously administered.

4. The method of claim 1, wherein the agent is administered at a dosage in the range of from 0.5 to 2.5 micrograms per kilogram of subject body weight.

5. A method for the treatment of priapism in a male subject suffering from priapism without raising the systemic blood pressure of said subject comprising administering to said subject a composition comprising a prostaglandin A1, prostaglandin B1, prostaglandin B2, or prostaglandin A2 in an amount which facilitates contraction of corpora cavernosa muscle in the cavernosum, without a concomitant rise in systemic blood pressure, for a time and under conditions that induce penile flaccidity or reduce the intensity of an erection.

6. The method of claim 5, wherein the prostaglandin is prostaglandin A2.

\* \* \* \* \*